United States Patent [19]

Hattori et al.

[11] Patent Number: 5,547,851
[45] Date of Patent: Aug. 20, 1996

[54] METHOD FOR MEASURING CARBON DIOXIDE AND REAGENT THEREFOR

[75] Inventors: Shizuo Hattori; Takahide Kishimoto; Yukihiro Sogabe; Shigenori Emi, all of Tsuruga, Japan

[73] Assignee: Toyo Boseki Kabushiki Kaisha, Tokyo, Japan

[21] Appl. No.: 210,559

[22] Filed: Mar. 18, 1994

[30] Foreign Application Priority Data

Mar. 22, 1993 [JP] Japan .................... 5-061987

[51] Int. Cl.$^6$ .................................................. C12Q 1/25
[52] U.S. Cl. ..................... 435/26; 435/822; 435/823; 435/25; 435/4
[58] Field of Search .................. 435/822, 823, 435/26, 25, 4

[56] References Cited

U.S. PATENT DOCUMENTS 3,974,037 8/1976 Adams ....................... 435/26

FOREIGN PATENT DOCUMENTS

0456444A2 11/1991 European Pat. Off. .
WO91/02082 2/1991 WIPO .

OTHER PUBLICATIONS

Gosselé et al. System. Appl. Microbiol. vol. 4, pp. 338–368 (1983).
Benziman, et al. J. Bacteriology vol. 98, No. 3, pp. 1005–1010 (1969), "Role of Phosphoenolpyruvate Carboxylation in *Acetobacter xylinum*".
Schwitzguebel et al., "Phosphenolpyruvate Carboxylase from *Acetobacter aceti*", Arch. Microbiol, 122, 109–115 (1979).

*Primary Examiner*—Carolyn Paden
*Attorney, Agent, or Firm*—Leydig, Voit & Mayer, Ltd.

[57] ABSTRACT

A method for measuring carbon dioxide, comprising the steps of: (1) reacting bicarbonate ion in a sample with phosphoenolpyruvate carboxylase derived from an acetic acid bacterium in the presence of phosphoenolpyruvate; (2) reacting the resultant oxalacetic acid with malate dehydrogenase in the presence of NADH; and (3) measuring decreased NADH, and a reagent for measuring carbon dioxide, comprising phosphoenolpyruvate, phosphoenolpyruvate carboxylase derived from an acetic acid bacterium, malate dehydrogenase, NADH and a buffer. According to the present invention, a highly stable reagent for $CO_2$ measurement, permitting a long-term storage in a liquid state can be provided by the use of phosphoenolpyruvate carboxylase derived from an acetic acid bacterium.

13 Claims, 5 Drawing Sheets

F I G. 1
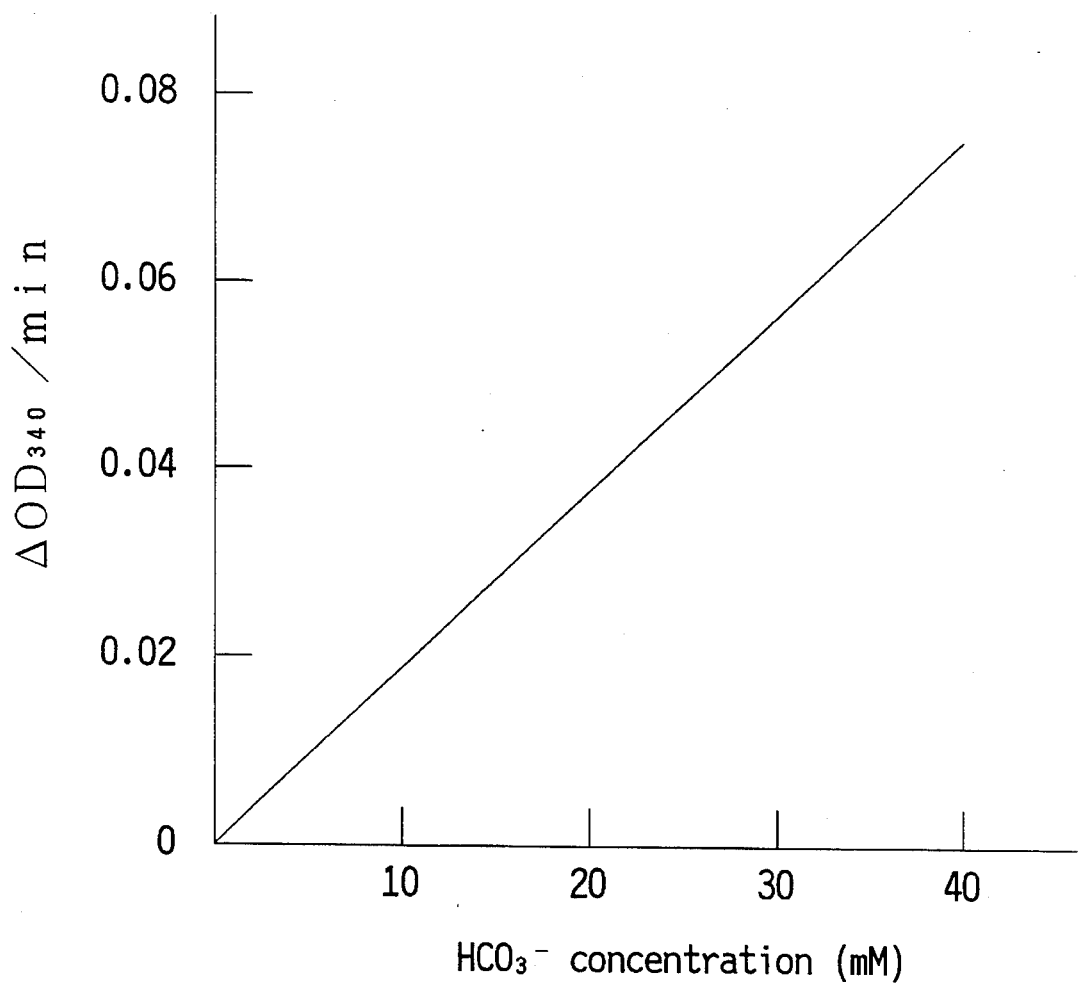

METHOD FOR MEASURING CARBON DIOXIDE AND REAGENT THEREFOR

FIELD OF THE INVENTION

The present invention relates to a method for measuring carbon dioxide in body fluids, particularly in blood serum or blood plasma, and to a reagent therefor.

BACKGROUND OF THE INVENTION

Carbon dioxide in blood serum or blood plasma is in an equilibrium with bicarbonate ion ($HCO_3^-$) and is a second largest fraction in blood serum or blood plasma. Therefore, the carbon dioxide forms the most important biological buffering action system in blood. Accordingly, measured values of the carbon dioxide content of blood serum or blood plasma are significant indices of electrolytic dispersion and shortage of anion, thus aiding medical diagnosis of acid-base inequilibrium in the respiratory system and metabolism. For example, normal bicarbonate ion concentration in blood serum and blood plasma is 22–32 mmol/l and a decrease to a low value of 15 mmol/l or an increase to a high value of 40 mmol/l indicates involvement of abnormality.

While carbon dioxide in body fluids can be measured by various methods, it is generally measured by tracing the changes caused by the enzyme reaction to be mentioned later. When phosphoenolpyruvate carboxylase is reacted with bicarbonate ion and phosphoenolpyruvic acid, oxalacetic acid and phosphoric acid are produced. The resultant oxalacetic acid is reacted with malate dehydrogenase in the presence of NADH and a decrease in NADH is measured by a known method such as an end point method or a rate method.

In the alkaline pH range, the equilibrium between carbon dioxide and bicarbonate ion shifts toward the direction to form bicarbonate ion and carbon dioxide exists as bicarbonate ion, and in the acidic pH range, it exists in the solution as $CO_2$ gas. For this reason, buffers having pH of 8.0 or above are generally used for a reagent for determining carbon dioxide.

The basic problem associated therewith is that phosphoenolpyruvate carboxylase is unstable at an alkaline pH, with the result that a reagent for carbon dioxide measurement containing this enzyme cannot be stored for a long time in a liquid state. The phosphoenolpyruvate carboxylases available in the market are mostly derived from plants such as maize leaves or wheat germ and show quite a poor stability at pH 8.0.

Incidentally, there is also known measurement of bicarbonate ion by the use of phosphoenolpyruvate carboxylase derived from Hyphomicrobium (EP 456444). This enzyme has a microbial origin and is free of the above-mentioned defects that the plant-originated phosphoenolpyruvate carboxylase has, and shows relatively high stability. It has been found, however, that the enzyme is not sufficiently stable at an enzyme concentration used for a reagent for measuring carbon dioxide (generally 0.05–5 U/ml).

In the measurement method as disclosed in U.S. Pat. No. 3,974,037, phosphoenolpyruvate carboxylase derived from *Escherichia coli* is used, though this enzyme shows poor stability in a reagent for measuring carbon dioxide which is weak alkaline.

Accordingly, a phosphoenolpyruvate carboxylase which is stable in a buffer (having a pH of about 8.0–8.5) to be used for the $CO_2$ measurement reagent is demanded.

SUMMARY OF THE INVENTION

As a result of the intensive studies, the present inventors have now found that a phosphoenolpyruvate carboxylase produced by an acetic acid bacterium is stable in a weak alkaline reagent for measuring carbon dioxide.

Accordingly, the present invention relates to a method for measuring carbon dioxide, comprising the steps of:

(1) reacting, in the presence of phosphoenolpyruvate, bicarbonate ion in a sample with phosphoenolpyruvate carboxylase derived from an acetic acid bacterium;

(2) reacting the resultant oxalacetic acid with malate dehydrogenase in the presence of NADH; and (3) measuring the decreased NADH.

In addition, the present invention relates to a reagent for measuring carbon dioxide, comprising phosphoenolpyruvate, phosphoenolpyruvate carboxylase derived from an acetic acid bacterium, malate dehydrogenase, NADH and a buffer.

BRIEF DESCRIPTION OF THE DRAWINGS

FIG. 1 shows the relation of the concentration of bicarbonate ion in a sample and a decrease in the absorbance of NADH per minute, which is caused by the use of the reagent of the present invention.

DETAILED DESCRIPTION OF THE INVENTION

Figure 2:
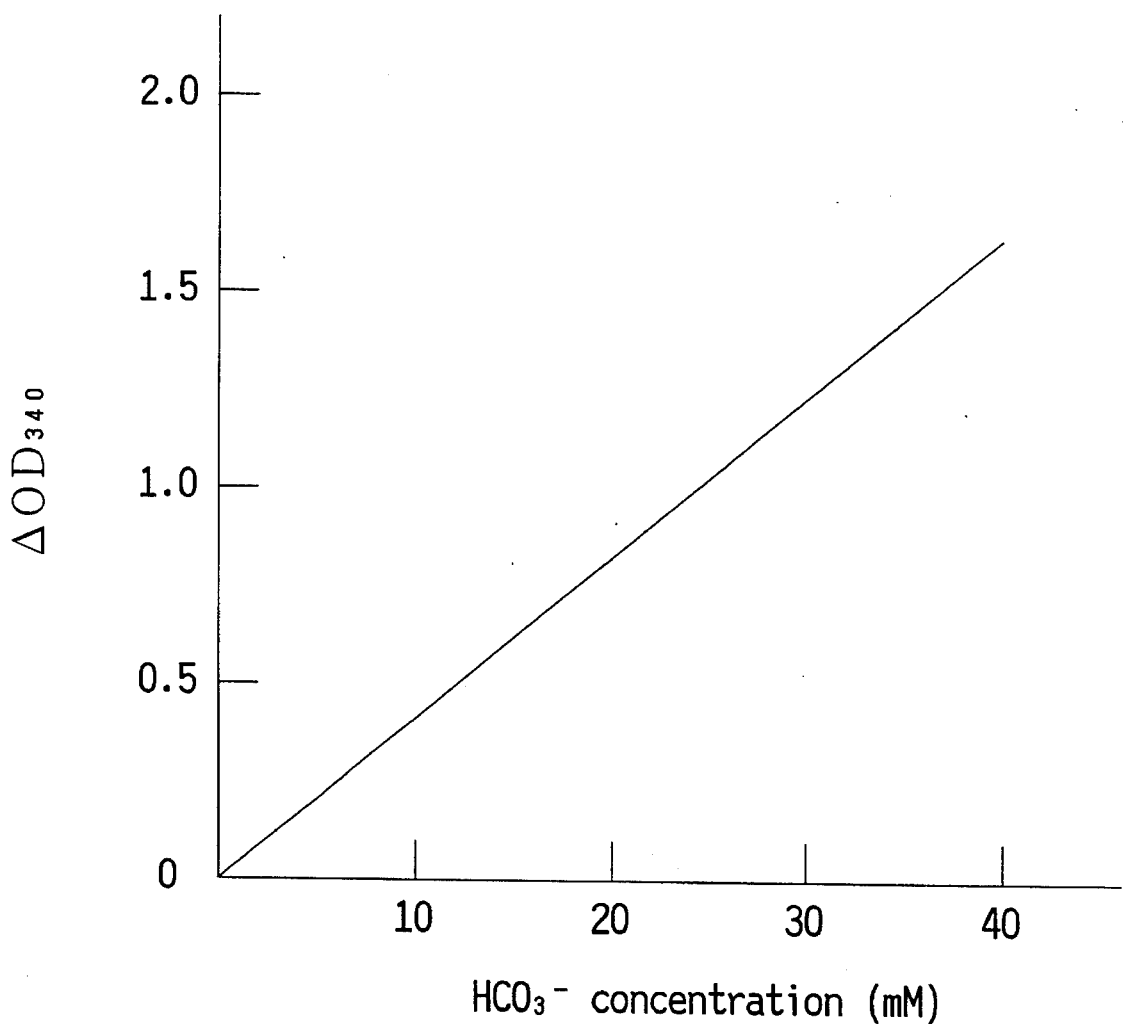
FIG. 2 shows the relation of the concentration of bicarbonate ion in a sample and a decrease in the absorbance of NADH in 5 minutes, which is caused by the use of the reagent of the present invention.

In the present invention, acetic acid bacteria mean the bacteria which oxidate ethyl alcohol to produce acetic acid.

The phosphoenolpyruvate carboxylase usable in the present invention can be obtained from almost all acetic acid bacteria, such as the genus Acetobacter, the genus Gluconobacter, the genus Frateuria and the genus Acidomonas. It is preferable from the economical point of view that a bacterium capable of yielding phosphoenolpyruvate carboxylase in a remarkably large amount should be used from among these bacteria. Preferred are the enzymes derived from *Acetobacter pasteurianus, Acetobacter xylinum, Acetobacter hansenii* or *Gluconobacter oxydans*. Specific examples thereof include enzymes derived from *Acetobacter hansenii* IFO 14820 (ATCC 35959), *Acetobacter pasteurianus* IFO 14814 (ATCC 23768), *Acetobacter xylinum* IFO 15237 (NCIB 11664) or *Gluconobacter oxydans* IFO 3462 (NRRL B-1225).

Of these, *Acetobacter hansenii* ATCC 35959 and *Acetobacter pasteurianus* ATCC 23768 are available from American Type Culture Collection, Rockville, Md., USA, *Acetobacter xylinum* NCIB 11664 is available from National Collection of Industrial and Marine Bacteria, Aberdeen, Scotland, United Kingdom; and *Gluconobacter oxydans*

NRRL B-1225 is available from Agricultural Research Service Culture Collection, Peoria, Ill., USA.

The phosphoenolpyruvate carboxylase produced by an acetic acid bacterium is reported in known literatures as being obtainable from, for example, *Acetobacter aceti* [Arch. Microbiol., 122, 109 (1979)] or *Acetobacter xylinum* [J. Bacteriol., 98, 1005 (1969)]. The phosphoenolpyruvate carboxylase to be used in the present invention is also obtainable by purification according to the methods described in those literatures.

Purification of phosphoenolpyruvate carboxylase which is suitably used in the present invention and is derived from *Acetobacter hansenii* is shown in the following.

For example, *Acetobacter hansenii* IFO 14820 (ATCC 35959) is cultured in a nutrient medium. After harvesting, the cells are suspended in 50 mM potassium phosphate buffer (pH 7.0) and crushed by a French press. After centrifugation, 30–50% ammonium sulfate fractions are obtained from the culture supernatant. The obtained enzyme solution is purified by ion-exchange chromatography, hydroxyapatite chromatography etc. to give an enzyme solution containing about 25 U/mg protein. This method is also applicable to the purification of phosphoenolpyruvate carboxylase yielded by other bacterium belonging to acetic acid bacteria.

The above-mentioned phosphoenolpyruvate carboxylase yielded by *Acetobacter hansenii* has the following physico-chemical properties.

Km value: 0.21 mM (for phosphoenolpyruvate)

Optimal pH: 7.5–8.0

Optimal temperature: 60° C.

Molecular weight: about 390,000 (gel filtration)

Not activated by acetyl CoA.

Not inhibited by ADP.

The activity of the phosphoenolpyruvate carboxylase can be determined according to the following method.

A reaction mixture (2.9 ml) containing 50 mM Tris-HCl, 10 mM $Na_2CO_3$, 3.2 mM phosphoenolpyruvic acid, 100 mM $MgSO_4$, 0.14 mM NADH and 50 U/ml malate dehydrogenase is prepared in a cuvette (d=1 cm) and preheated at 30° C. for about 5 minutes. An enzyme solution (0.1 ml) is added thereto and gently mixed. A change in absorbance at 340 nm is recorded for 2–3 minutes with a spectrophotometer with water adjusted to 30° C. as a control, and change in absorbance per minute is calculated from the initial linear portion thereof (ΔOD test). A blank test is performed by using 50 mM phosphate buffer (pH 7.0) in place of the enzyme solution and following the same steps to determine change in absorbance per minute (ΔOD blank). The activity of phosphoenolpyruvate carboxylase is calculated by taking the enzyme amount consuming 1 micromole NADH in a minute under the above conditions as 1 unit (U).

Examples of the phosphoenolpyruvate to be used in the present invention include potassium salt, sodium salt, tricyclohexylammonium salt and monocyclohexylammonium salt.

Examples of the malate dehydrogenase usable in the present invention include those derived from swine heart, the genus Thermus and the genus Bacillus.

The buffer to be used in the present invention may be any insofar as it is weak alkaline (pH 8.0–8.5). Examples include Tris-HCl buffer, Tricine-HCl buffer and Good's buffer.

The method for measuring carbon dioxide follows the reactions shown by the formulas below.

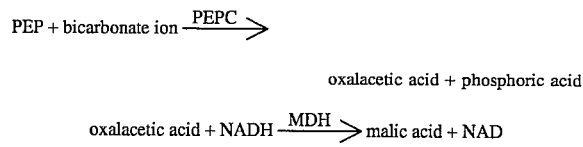

wherein PEP is phosphoenolpyruvate, PEPC is phosphoenolpyruvate carboxylase and MDH is malate dehydrogenase.

Besides the phosphoenolpyruvate carboxylase derived from an acetic acid bacterium, the reagent for $CO_2$ measurement of the present invention should contain phosphoenolpyruvate. The bicarbonate ion in the reagent generally produces oxalacetic acid from phosphoenolpyruvic acid by the action of the aforesaid phosphoenolpyruvate carboxylase under weak alkaline conditions. The oxalacetic acid is quantitatively determined by the use of malate dehydrogenase in the presence of NADH, from the decrease of NADH which is caused by the production of malic acid from the oxalacetic acid. An end point method or a rate method is usable for this end.

The measurement of carbon dioxide is conducted under weak alkaline conditions generally at pH 7.5–9.0, preferably 8.0–8.5.

The reagent of the present invention preferably contains 3–100 mM bivalent cation such as magnesium ion ($Mg^{2+}$) or manganese ion ($Mn^{2+}$) as a cofactor, with preference given to magnesium ion. Examples of the substances producing such bivalent cations include salts such as magnesium sulfate, magnesium chloride, manganese sulfate and manganese chloride.

The reagent of the present invention generally has the following formulation.

| | |
|---|---|
| Weak alkaline buffer | 10–50 mM |
| Phosphoenolpyruvate | 2–5 mM |
| Magnesium ion | 3–100 mM |
| NADH | 0.3–1.5 mM |
| Malate dehydrogenase | 5–50 U/ml |
| Phosphoenolpyruvate carboxylase derived from acetic acid bacterium | 0.5–10 U/ml |

More specifically, the following formulation is exemplified.

| | |
|---|---|
| Tris-HCl buffer (pH 8.0) | 10–50 mM |
| Magnesium sulfate | 3–100 mM |
| Potassium phosphoenolpyruvate | 2–5 mM |
| NADH | 0.3–1.5 mM |
| Malate dehydrogenase | 5–50 U/ml |
| Phosphoenolpyruvate carboxylase derived from acetic acid bacterium | 0.5–5 U/ml |

So as to inhibit an interfering reaction by lactate dehydrogenase and pyruvic acid in a sample, addition of a lactate dehydrogenase inhibitor such as oxamate (e.g. sodium oxamate) at about 1–20 mM is desirable.

The above-mentioned reagent (1.5–3.0 ml) and a sample (0.01 ml) containing bicarbonate ion are mixed and allowed to react at 37° C. for 5–10 minutes, and decrease in absorbance at, for example, 340 nm, 365 nm or 380 nm is measured according to NADH concentration.

The above-mentioned formulation is for the end point method and for the rate method, the following is generally suitable.

| | |
|---|---|
| Weak alkaline buffer | 10–50 mM |
| Phosphoenolpyruvate | 2–5 mM |
| Magnesium ion | 3–100 mM |
| NADH | 0.1–0.2 mM |
| Malate dehydrogenase | 5–50 U/ml |
| Phosphoenolpyruvate carboxylase derived from acetic acid bacterium | 0.05–1 U/ml |

More specifically, the following formulation is exemplified.

| | |
|---|---|
| Tris-HCl buffer (pH 8.0) | 10–50 mM |
| Magnesium sulfate | 3–100 mM |
| Potassium phosphoenolpyruvate | 2–5 mM |
| NADH | 0.1–0.2 mM |
| Malate dehydrogenase | 5–50 U/ml |
| Phosphoenolpyruvate carboxylase derived from acetic acid bacterium | 0.05–0.5 U/ml |

It is also preferable to add a lactate dehydrogenase inhibitor such as oxamate (e.g. sodium oxamate) at about 1–20 mM for the same reason as mentioned for the end point method.

The phosphoenolpyruvate carboxylase derived from an acetic acid bacterium to be used in the present invention is superior in stability in the weak alkaline range as compared with phosphoenolpyruvate carboxylase of other origin which is used in conventional methods.

Acetic acid bacteria grow well in the range from neutral to acidic and grow even at pH 2.0–3.0. The enzymes yielded thereby is also stable in the similar pH range and considered to be unstable in the weak alkaline range. Hence, it is beyond expectation that the phosphoenolpyruvate carboxylase derived from an acetic acid bacterium is stable in a weak alkaline reagent for measuring carbon dioxide.

According to the present invention, a highly stable reagent for $CO_2$ measurement, permitting a long-term storage in a liquid state, can be provided by the use of phosphoenolpyruvate carboxylase derived from an acetic acid bacterium.

When an enzyme of other conventionally-used origin is employed, its activity is degraded at a concentration used for a reagent for measuring carbon dioxide (about 3 U/ml) by 5% even after the storage at 9° C. for 7 days and is completely deactivated after the storage at 25° C. for 7 days, as can be seen from the Comparative Example to be described later. In contrast, the enzyme of the present invention retains nearly 100% activity after the storage at 9° C. for 7 days and shows residual activity even after the storage at 25° C. for 7 days.

The present invention is described in detail by illustration of Examples, to which the invention is not limited.

REFERENCE EXAMPLE 1

*Acetobacter hansenii* IFO 14820 (ATCC 35959) was cultured in a nutrient medium containing polypeptone (0.5%), yeast extract (0.5%), glucose (0.5%) and magnesium sulfate (0.05%) at 30° C. for 2 days with aeration and the cells were crushed with a French press. After sulfate fractionation, the cells were purified by DEAE-Sepharose chromatography and hydroxyapatite chromatography to give phosphoenolpyruvate carboxylase standard enzyme product (specific activity 25 U/mg).

EXAMPLE 1

Using the phosphoenolpyruvate carboxylase standard enzyme product derived from *Acetobacter hansenii* IFO 14820 (ATCC 35959) as purified in Reference Example 1, the following reagent for measuring carbon dioxide was prepared.

| | |
|---|---|
| Tris-HCl buffer (pH 8.0) | 50 mM |
| Magnesium sulfate | 10 mM |
| Potassium phosphoenolpyruvate | 3.2 mM |
| NADH | 0.14 mM |
| Malate dehydrogenase | 50 U/ml |
| Phosphoenolpyruvate carboxylase | 0.3 U/ml |

The above-mentioned reagent (3.0 ml) and a sample (0.01 ml) containing bicarbonate ion (0–40 mM) were mixed and allowed to react at 37° C. for 3 minutes and decrease in absorbance at 340 nm was measured (the value at bicarbonate ion concentration of 0 mM was subtracted as a blank value) (rate method). The relation of the concentration of bicarbonate ion in the sample and decrease in the absorbance per minute is shown in FIG. 1. A linear relation existed between the concentration of bicarbonate ion and the change in absorbance.

EXAMPLE 2

Using the phosphoenolpyruvate carboxylase standard enzyme product derived from *Acetobacter hansenii* IFO 14820 (ATCC 35959) as purified in Reference Example 1, the following reagent for measuring carbon dioxide was prepared.

| | |
|---|---|
| Tris-HCl buffer (pH 8.0) | 50 mM |
| Magnesium sulfate | 10 mM |
| Potassium phosphoenolpyruvate | 3.2 mM |
| NADH | 0.5 mM |
| Malate dehydrogenase | 50 U/ml |
| Phosphoenolpyruvate carboxylase | 3 U/ml |

The above-mentioned reagent (3.0 ml) and a sample (0.01 ml) containing bicarbonate ion (0–40 mM) were mixed and allowed to react at 37° C. for 5 minutes and decrease in absorbance at 340 nm in 5 minutes was measured (the value at bicarbonate ion concentration of 0 mM was subtracted as a blank value) (end point method). The relation of the concentration of bicarbonate ion in the sample and decrease in the absorbance in 5 minutes is shown in FIG. 2. A linear relation existed between the concentration of bicarbonate ion and the change in absorbance.

EXAMPLE 3

Figure 3:
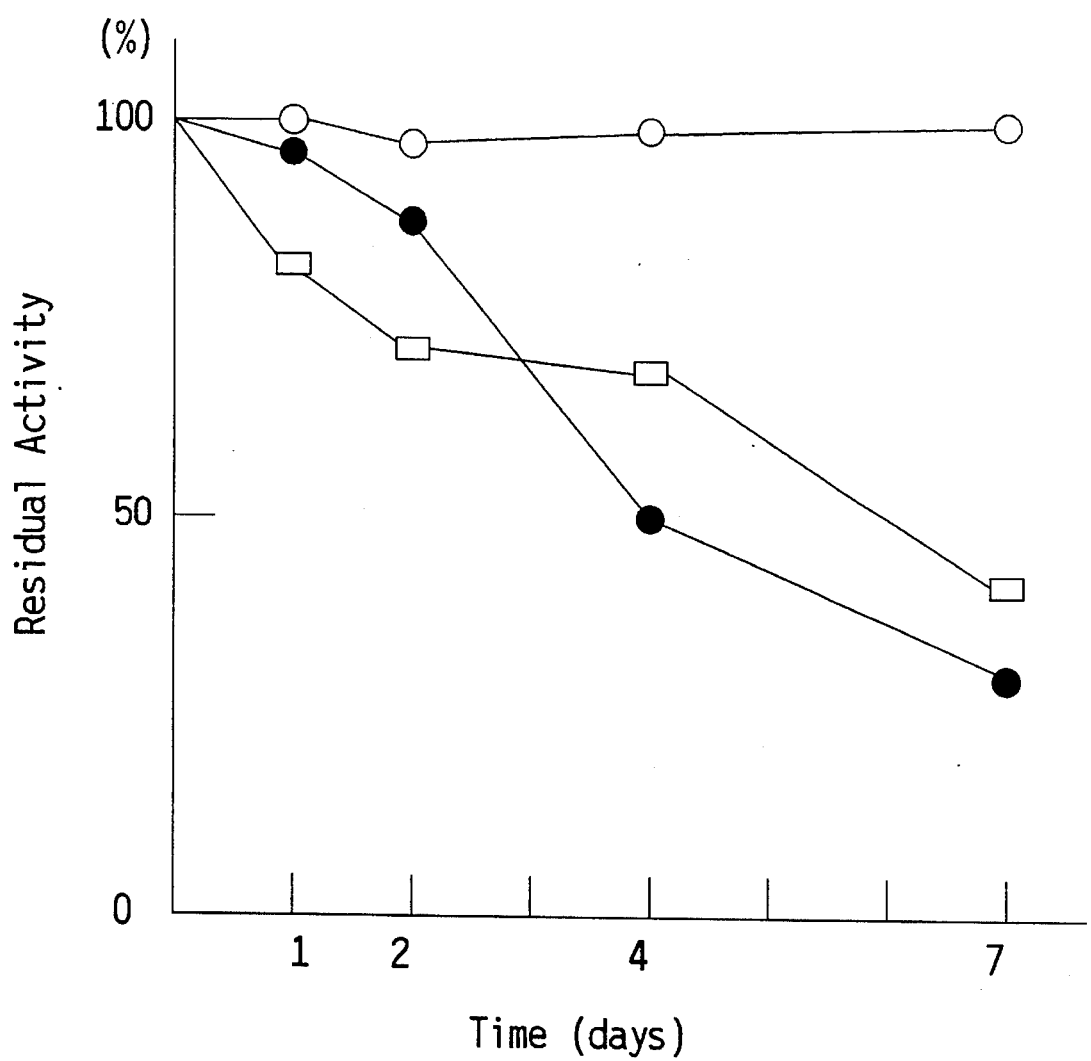
FIG. 3 shows the preservation stability of the reagent of the present invention, wherein o is at 9° C., ● is at 25° C. and □ is at 40° C.

The reagent for measuring carbon dioxide as obtained in Example 2 was preserved at 9° C., 25° C. or 40° C. and the activity of phosphoenolpyruvate carboxylase in the reagent was measured at day 0, day 1, day 2, day 4 and day 7. The results are shown in FIG. 3. After preservation for 7 days, the residual activity was 100% (9° C.), 31% (25° C.) and 41% (40° C.).

COMPARATIVE EXAMPLE 1

Figure 4:
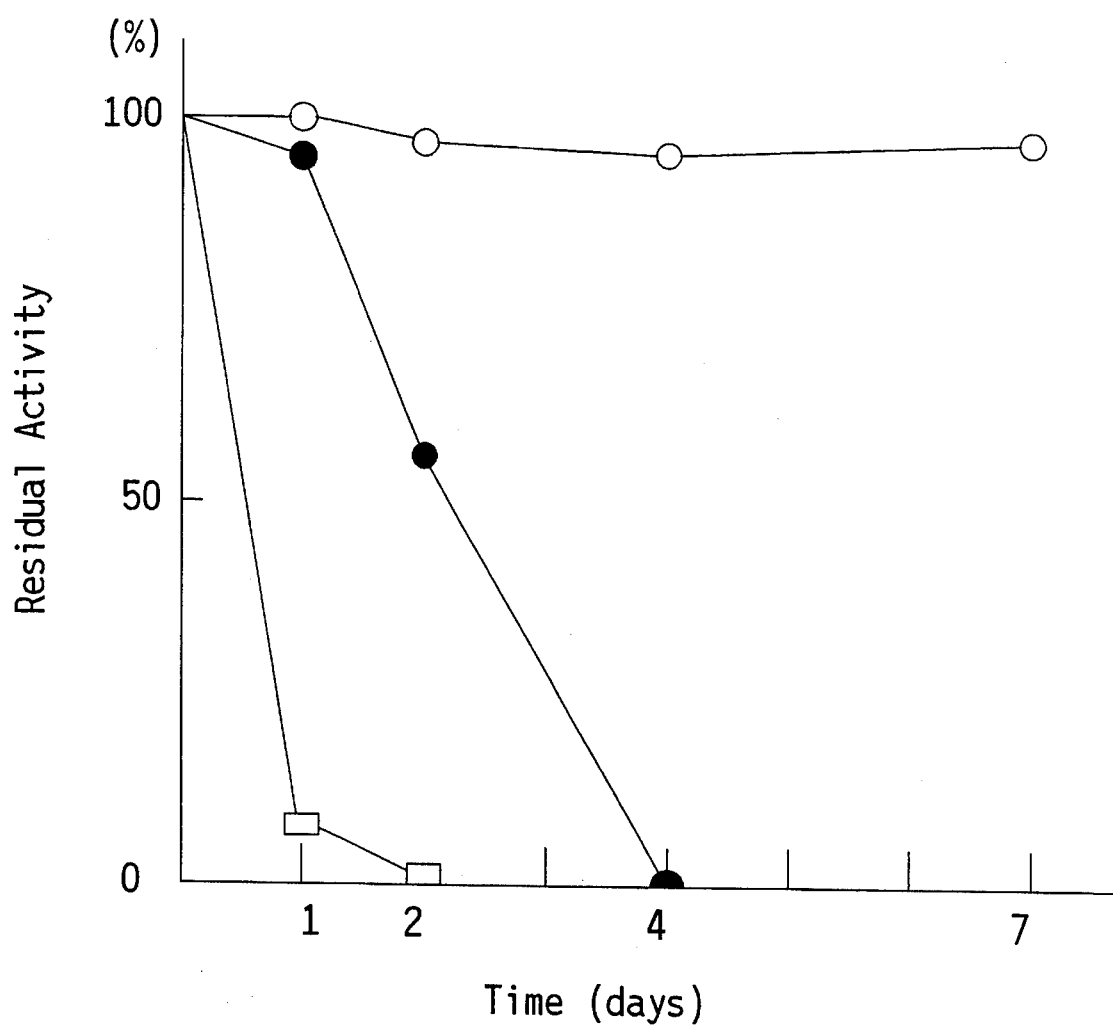
FIG. 4 shows the preservation stability of a reagent for comparison, wherein o is at 9° C., ● is at 25° and □ is at 40°.

Using phosphoenolpyruvate carboxylase derived from maize leaves (Biozyme), a reagent for measuring carbon dioxide which had the same formulation as the reagent of Example 2 was prepared. The reagent was preserved at 9° C., 25° C. or 40° C. and the enzyme activity was measured at day 0, day 1, day 2, day 4 and day 7. The results are shown in FIG. 4. After preservation for 7 days, the residual activity was 20% (9° C.), 0% (25° C.) and 0% (40° C.).

The enzyme derived from corn showed inferior stability as compared with the enzyme derived from an acetic acid bacterium.

REFERENCE EXAMPLE 2

*Hyphomicrobium methylovorum* IFO 14180 was cultured in a nutrient medium containing methanol (1.0%), diammonium phosphate (0.3%), dipotassium phosphate (0.2%), sodium chloride (0.2%), magnesium sulfate (0.02%) and various vitamins at 30° C. for 4 days and the cells were crushed with a French press. After sulfate fractionation, the cells were purified by DEAE-Sepharose chromatography and hydroxyapatite chromatography to give a phosphoenolpyruvate carboxylase standard enzyme product (specific activity 20 U/mg).

COMPARATIVE EXAMPLE 2

Using the phosphoenolpyruvate carboxylase obtained in Reference Example 2, a reagent for measuring carbon dioxide which had the same formulation as the reagent of Example 2 was prepared. The reagent was preserved at 9° C., 25° C. or 40° C. and the enzyme activity was measured at day 0, day 1, day 4 and day 7.

Figure 5:
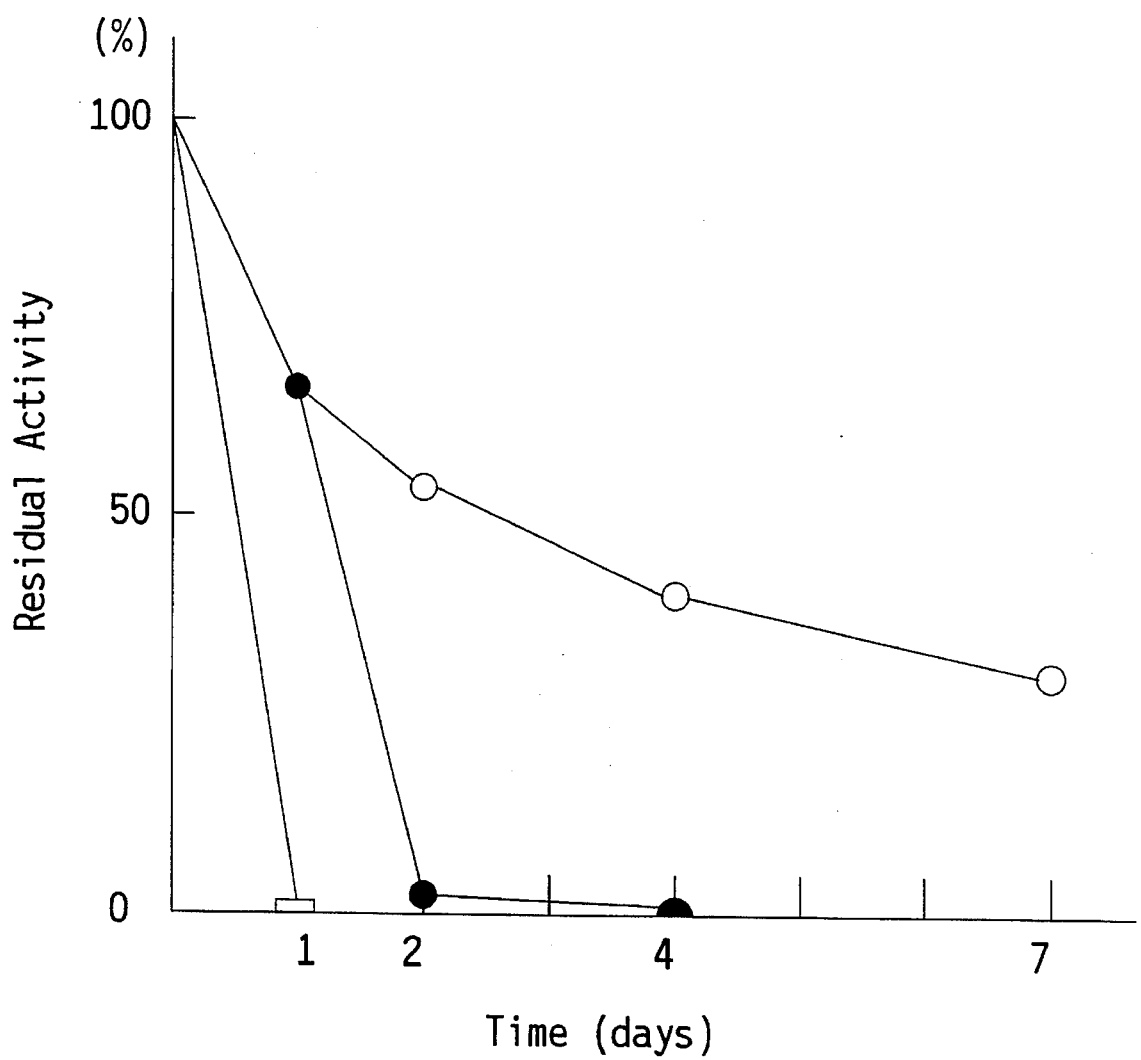
FIG. 5 shows the preservation stability of a reagent for comparison, wherein o is at 9° C., ● is at 25° C. and □ is at 40°.

The results are shown in FIG. 5. After preservation for 7 days, the residual activity was 95% (9° C.), 0% (25° C.) and 0% (40° C.). The enzyme derived from Hyphomicrobium showed inferior stability as compared with the enzyme derived from an acetic acid bacterium.

COMPARATIVE EXAMPLE 3

According to the method described in U.S. Pat. No. 3,974,037, phosphoenolpyruvate carboxylase derived from *Escherichia coli* was purified. Using said enzyme, a reagent for measuring carbon dioxide which had the same formulation as the reagent of Example 2 was prepared. Acetyl CoA was added to the reagent (1 mM). The reagent was preserved at 25° C. and the enzyme activity was measured at day 0 and day 4. The residual activity at day 4 was 4%. The enzyme derived from *Escherichia coli* showed inferior stability as compared with the enzyme derived from an acetic acid bacterium.

EXAMPLE 4

*Acetobacter pasteurianus* IFO 14814 (ATCC 23768) was cultured in a nutrient medium and purified by a known method to give a phosphoenolpyruvate carboxylase standard enzyme product (specific activity 25 U/mg). Using said standard product, a reagent for measuring carbon dioxide which had the same formulation as the reagent of Example 2 was prepared. The concentration of magnesium sulfate was 100 mM. In the same manner, enzyme products were prepared from *Acetobacter xylinum* IFO 15237 (NCIB 11664) and *Gluconobacter oxydans* IFO 3462 (NRRL B-1225) and prepared into reagents for $CO_2$ measurement.

The reagents were preserved at 9° C., 25° C. or 40° C. and the enzyme activity was measured at day 0, day 1, day 2, day 4 and day 7. The results are shown in Table 1. All reagents showed higher stability as compared with the reagents obtained from conventional enzymes.

TABLE 1

| Storage time | Residual activity in reagents for measuring carbon dioxide | | | | | | | | |
|---|---|---|---|---|---|---|---|---|---|
| | A. Pasteurianus | | | A. xylinum | | | G. oxydans | | |
| | 9° C. | 25° C. | 40° C. | 9° C. | 25° C. | 40° C. | 9° C. | 25° C. | 40° C. |
| Day 0 | 100% | 100% | 100% | 100% | 100% | 100% | 100% | 100% | 100% |
| Day 1 | 102% | 99% | 86% | 102% | 100% | 92% | 100% | 98% | 15% |
| Day 2 | 100% | 83% | 80% | 100% | 78% | 80% | 101% | 55% | 5% |
| Day 4 | 100% | 62% | 75% | 100% | 44% | 60% | 99% | 30% | 0% |
| Day 7 | 99% | 54% | 66% | 101% | 21% | 35% | 99% | 10% | 0% |

The stability of phosphoenolpyruvate carboxylase derived from an acetic acid bacterium or other origin in a reagent for measuring carbon dioxide (pH 8.0) was compared based on the residual activity after preservation at 25° C. for 4 days. The results are shown in Table 2.

TABLE 2

| Origin | Stability in reagent for measuring carbon dioxide (25° C., 4 days) Residual activity |
|---|---|
| Acetobacter hansenii | 50% |
| Acetobacter pasteurianus | 62% |
| Acetobacter xylinum | 44% |
| Gluconobacter oxydans | 30% |
| Maize leaves | 0% |
| Hyphomicrobium methylovorum | 0% |
| Escherichia coli | 4% |

It is evident that the reagent of the present invention is superior in stability as compared with conventional reagents for measuring carbon dioxide.

What is claimed is:

1. A method for measuring bicarbonate ion in a liquid sample, comprising the steps of:

(1) reacting said bicarbonate ion in said sample with phosphoenolpyruvate carboxylase derived from *Acetobacter hansenii* and phosphoenolpyruvate;

(2) reacting the resultant oxalacetic acid with malate dehydrogenase and NADH; and (3) measuring; wherein said NADH measurement correlates with said bicarbonate ion measurement.

2. The method of claim 1, wherein the phosphoenolpyruvate carboxylase is derived from *Acetobacter hansenii* ATCC 35959.

3. The method of claim 1, wherein said reacting steps (1) and (2) are each carried out in a buffer having a pH of 8.0–8.5.

4. The method of claim 1, wherein said reacting includes magnesium ion.

5. The method of claim 1, wherein the step of measuring NADH is accomplished by measuring absorbance of a reaction mixture.

6. The method of claim 1, wherein said liquid sample is a body fluid.

7. The method of claim 6, wherein said body fluid is blood serum or blood plasma.

8. A composition comprising phosphoenolpyruvate, phosphoenolpyruvate carboxylase derived from *Acetobacter hansenii*, malate dehydrogenase, NADH and a buffer.

9. The composition of claim 8, wherein the phosphoenolpyruvate carboxylase is derived from *Acetobacter hansenii* ATCC 35959.

10. The composition of claim 8, having a pH of 8.0–8.5.

11. The composition of claim 8, further comprising magnesium ions.

12. The composition of claim 8, comprising 10–50 mM weak alkaline buffer, 2–5 mM phosphoenolpyruvate, 3–100 mM magnesium ions, 0.3–1.5 mM NADH, 5–50 U/ml malate dehydrogenase and 0.5–10 U/ml phosphoenolpyruvate carboxylase derived from *Acetobacter hansenii*.

13. The composition of claim 8, comprising 10–50 mM weak alkaline buffer, 2–5 mM phosphoenolpyruvate, 3–100 mM magnesium ions, 0.1–0.2 mM NADH, 5–50 U/ml malate dehydrogenase and 0.05–1 U/ml phosphoenolpyruvate carboxylase derived from *Acetobacter hansenii*.

* * * * *

UNITED STATES PATENT AND TRADEMARK OFFICE
CERTIFICATE OF CORRECTION

PATENT NO. : 5,547,851
DATED : August 20, 1996
INVENTOR(S) : Hattori et al.

It is certified that error appears in the above-identified patent and that said Letters Patent is hereby corrected as shown below:

In Column 4, line 4: The text should be aligned with the text in line 2.

Signed and Sealed this

Eighteenth Day of February, 1997

Attest:

BRUCE LEHMAN

*Attesting Officer*  *Commissioner of Patents and Trademarks*